(12) United States Patent
Kimm et al.

(10) Patent No.: US 9,114,219 B2
(45) Date of Patent: Aug. 25, 2015

(54) INSUFFLATING-EXSUFFLATING SYSTEM

(75) Inventors: Gardner Kimm, Carlsbad, CA (US); Smita Garde, Irvine, CA (US); Mabini Arcilla, San Diego, CA (US); Samir Ahmad, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1020 days.

(21) Appl. No.: 13/129,887

(22) PCT Filed: Oct. 29, 2009

(86) PCT No.: PCT/IB2009/054810
§ 371 (c)(1),
(2), (4) Date: May 18, 2011

(87) PCT Pub. No.: WO2010/058308
PCT Pub. Date: May 27, 2010

(65) Prior Publication Data
US 2011/0220107 A1  Sep. 15, 2011

Related U.S. Application Data

(60) Provisional application No. 61/116,055, filed on Nov. 19, 2008.

(51) Int. Cl.
*F16K 31/02* (2006.01)
*A61M 16/00* (2006.01)
*A61M 16/10* (2006.01)

(52) U.S. Cl.
CPC ........... *A61M 16/00* (2013.01); *A61M 16/0006* (2014.02); *A61M 16/0009* (2014.02); *A61M 16/0051* (2013.01); *A61M 2016/0027* (2013.01); *A61M 2016/0039* (2013.01); *A61M 2016/0042* (2013.01); *A61M 2016/102* (2013.01); *A61M 2205/3584* (2013.01); *A61M 2205/502* (2013.01); *A61M 2205/52* (2013.01); *A61M 2230/43* (2013.01); *A61M 2230/46* (2013.01)

(58) Field of Classification Search
USPC ............. 128/204.18, 204.21, 204.23, 205.12, 128/205.15, 205.19, 207.14
See application file for complete search history.

(56) References Cited

U.S. PATENT DOCUMENTS

| | | | |
|---|---|---|---|
| 4,821,709 A | 4/1989 | Jensen | |
| 6,929,007 B2 * | 8/2005 | Emerson | 128/205.12 |
| 2004/0069304 A1 | 4/2004 | Jam | |
| 2007/0017522 A1 | 1/2007 | Be'Eri | |
| 2007/0113843 A1 | 5/2007 | Hughes | |
| 2007/0186928 A1 * | 8/2007 | Be'Eri | 128/204.18 |
| 2007/0199566 A1 * | 8/2007 | Be'eri | 128/204.23 |
| 2008/0023005 A1 * | 1/2008 | Tokunaga | 128/205.19 |

FOREIGN PATENT DOCUMENTS

| | | |
|---|---|---|
| CN | 1849150 A | 10/2006 |
| WO | 0047258 A1 | 8/2000 |
| WO | 2007054829 A2 | 5/2007 |

* cited by examiner

*Primary Examiner* — Steven Douglas
*Assistant Examiner* — Kathrynn Reilly

(57) ABSTRACT

A system (10) and method of insufflating-exsufflating a subject (12) that enables monitoring and/or control over an enhanced set of breathing parameters during insufflation-exsuffiation. The system and/or method may include automatic triggering and/or notification to a caregiver of insuffla-tion-exsuffiation. The insufflation-exsuffiation of the subject may be preceded by a secretion loosing routine that loosens secretions in the airway of the subject without moving the loosened secretions up the airway.

20 Claims, 3 Drawing Sheets

INSUFFLATING-EXSUFFLATING SYSTEM

CROSS REFERENCE TO APPLICATIONS

This application is a U.S. national phase of International Application No. PCT/IB2009/054810, filed Oct. 29, 2009, which designated the U.S. and claims the benefit of U.S. Provisional Application No. 61/116,065, filed Nov. 19, 2008, each of which is incorporated herein by reference in its entirety.

BACKGROUND OF THE INVENTION

1. Field of the Invention

The invention relates to the insufflation-exsufflation system, and, in particular, to a system that of a patient.

2. Description of the Related Art

Systems for insufflating-exsufflating ventilation patients to remove secretions that accumulate in the airway are known. Generally, these systems are separate from a ventilation system being used to ventilate a patient, and the patient must be manually disconnected from the ventilation system, connected to the insufflation-exsufflation system, insufflate-exsufflated, and then reattached to the ventilation system.

Conventional insufflation-exsufflation systems tend to be relatively rudimentary devices that require manual operation and provide little to no control over the flow of gas to and from the patient during insufflation-exsufflation. For example, a typical insufflation-exsufflation system will provide an interface that enables a user (e.g., a caregiver) to initiate an insufflation-exsufflation cycle in which a positive pressure is applied to the airway of the patient for a predetermined time to insufflate the patient and then a negative pressure is applied to the airway of the patient for a predetermined time to exsufflate the patient. The predetermined timings and a maximum and minimum pressure are usually the only parameters of the delivery of gas to, or the drawing of gas away from, the airway of the patient that are configurable by the user. Other parameters of gas within the airway of the patient during insufflation-exsufflation (e.g., flow waveform shape, maximum flow, respiratory volume, etc.) cannot be controlled by the user to optimize therapy.

SUMMARY OF THE INVENTION

One aspect of the invention relates to a system configured to extract secretions from the airway of a subject. In one embodiment, the system comprises a circuit, and a processor. The circuit is configured to control the pressure at the airway of a subject by generating a flow of gas having a controlled pressure that is delivered to the airway of the subject by an airway interface circuit that communicates the circuit with the airway of the subject. The processor is configured to control the circuit such that the flows of gas generated by the circuit move secretions up the airway of the subject by (i) fluctuating the pressure in the airway of the subject up and down for a plurality of loosening cycles such that the fluctuation of the pressure in the airway of the subject during the loosening cycles loosens secretions in the airway of the subject without moving the secretions up the airway of the subject, and (ii) fluctuating the pressure in the airway of the subject up and down for one or more insufflation-exsufflation cycles such that a given insufflation-exsufflation cycle insufflates and exsufflates the patient, thereby moving secretions up the airway of the subject.

Another aspect of the invention relates to a method of extracting secretions from the airway of a subject. In one embodiment, the method comprises loosening secretions within the airway of a subject without extracting amounts of secretions by delivering gas to the airway of the subject such that pressure in the airway of the subject is fluctuated up and down for a plurality of loosening cycles; and insufflating-exsufflating the subject to extract secretions from the airway of the patient by delivering gas to the airway of the subject such that pressure in the airway alternates the pressure in the airway of the subject between positive pressure and negative pressure for one or more insufflation-exsufflation cycles, thereby extracting secretions from the airway of the subject.

Yet another aspect of the invention relates to a system configured to extract secretions from the airway of a subject. In one embodiment, the system comprises means for loosening secretions within the airway of a subject without extracting amounts of secretions by delivering gas to the airway of the subject such that pressure in the airway of the subject is fluctuated up and down for a plurality of loosening cycles; and means for insufflating-exsufflating the subject to extract secretions from the airway of the patient by delivering gas to the airway of the subject such that pressure in the airway alternates the pressure in the airway of the subject between positive pressure and negative pressure for one or more insufflation-exsufflation cycles, thereby extracting secretions from the airway of the subject.

Still another aspect of the invention relates to a system configured to insufflate-exsufflate a subject. In one embodiment, the system comprises a circuit, one or more sensors, and a processor. The circuit is configured to control the pressure at the airway of a subject by generating a flow of gas having a controlled pressure that is delivered to the airway of the subject by an airway interface circuit that communicates the circuit with the airway of the subject. The one or more sensors are in communication with gas within the circuit, and generate output signals conveying information related to one or more additional parameters of the gas within the circuit in addition to information related to the pressure of the gas within the circuit. The processor is configured to control the circuit to insufflate-exsufflate the subject, wherein the processor receives the output signals generated by the one or more sensors and implements information conveyed in one or more output signals related to the one or more additional parameters of the gas within the circuit in controlling the circuit during insufflation-exsufflation.

Yet another aspect of the invention relates to a method of insufflating-exsufflating a subject. In one embodiment, the method comprises controlling the flow of gas in the airway of a patient to insufflate-exsufflate the subject, wherein the flow of gas in the airway of the patient is controlled by a circuit configured to control the pressure at the airway of a subject by generating a flow of gas having a controlled pressure that is delivered to the airway of the subject by an airway interface circuit that communicates the circuit with the airway of the subject; monitoring one or more additional parameters of the gas within the circuit in addition to information related to the pressure of the gas within the circuit; and adjusting the operation of the circuit during the insufflation-exsufflation of the subject based on the one or more additional parameters of the gas within the circuit.

Still another aspect of the invention relates to a system configured to insufflate-exsufflate a subject. In one embodiment, the system comprises means for controlling the flow of gas in the airway of a patient to insufflate-exsufflate the subject, wherein the flow of gas in the airway of the patient is controlled by one or more additional parameters of the gas within the circuit in addition to information related to the pressure of the gas within the circuit; means for monitoring one or more additional parameters of the gas within the circuit in addition to information related to the pressure of the gas within the circuit; and means for adjusting the operation of the circuit during the insufflation-exsufflation of the subject based on the one or more additional parameters of the gas within the circuit.

Yet another aspect of the invention relates to a system configured to insufflate-exsufflate a subject. In one embodiment the system comprises a circuit and a processor. The circuit is configured to control the pressure at the airway of a subject by generating a flow of gas having a controlled pressure that is delivered to the airway of the subject by an airway interface circuit that communicates the circuit with the airway of the subject. The processor configured to determine a baseline measurement for one or more key parameters of gas in the respiratory system of the subject, and to control the circuit to insufflate-exsufflate the subject such that the one or more key parameters of the gas in the respiratory system of the subject do not breach the baseline measurement.

Still another aspect of the invention relates to a method of insufflating-exsufflating a subject. In one embodiment, the method comprises determining a baseline measurement for one or more key parameters of gas in the respiratory system of a subject; and insufflating-exsufflating the subject such that the one or more key parameters of the gas in the respiratory system of the subject do not breach the baseline measurement during the insufflation-exsufflation.

Yet another aspect of the invention relates to a system configured to insufflate-exsufflate a subject. In one embodiment, the system comprises means for determining a baseline measurement for one or more key parameters of gas in the respiratory system of a subject; and means for insufflating-exsufflating the subject such that the one or more key parameters of the gas in the respiratory system of the subject do not breach the baseline measurement during the insufflation-exsufflation.

Still another aspect of the invention relates to a system configured to insufflate-exsufflate a subject. In one embodiment the system comprises a circuit, one or more sensors, and a processor. The circuit configured to control the pressure at the airway of a subject by generating a flow of gas having a controlled pressure that is delivered to the airway of the subject by an airway interface circuit that communicates the circuit with the airway of the subject. The sensors are configured to generate one or more output signals that convey information related to one or more parameters of gas within the airway of the subject. The processor is configured to receive the one or more output signals, and to control the circuit to insufflate-exsufflate the subject. In some instances, the processor comprises a secretion detection module, and an inexsufflation module. The secretion detection module is configured to monitor the information related to one or more parameters of the gas within the airway of the subject and to identify an accumulation of secretions in the airway of the subject based on the information related to one or more parameters of the gas within the airway of the subject. The inexsufflation module is configured to control the circuit to commence an insufflation-exsufflation routine that insufflate-exsufflates the subject based on identifications of accumulated secretions in the airway of the subject by the secretion detection module such that identification of secretions in the airway of the subject by the secretion detection module trigger inexsufflation module to control the circuit to commence an insufflation-exsufflation routine without intervention from a user.

Yet another aspect of the invention relates to a method of insufflating-exsufflating a subject. In one embodiment, the method comprises monitoring one or more parameters of the gas within the airway of a subject; automatically identifying an accumulation of secretions in the airway of the subject based on the one or more parameters of the gas within the airway of the subject; and triggering an insufflation-exsufflation routine that insufflate-exsufflates the subject based on the identification of accumulated secretions in the airway of the subject without intervention from a user.

Still another aspect of the invention relates to a system configured to insufflate-exsufflate a subject. In one embodiment the system comprises means for monitoring one or more parameters of the gas within the airway of a subject; means for automatically identifying an accumulation of secretions in the airway of the subject based on the one or more parameters of the gas within the airway of the subject; and means for triggering an insufflation-exsufflation routine that insufflate-exsufflates the subject based on the identification of accumulated secretions in the airway of the subject without intervention from a user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
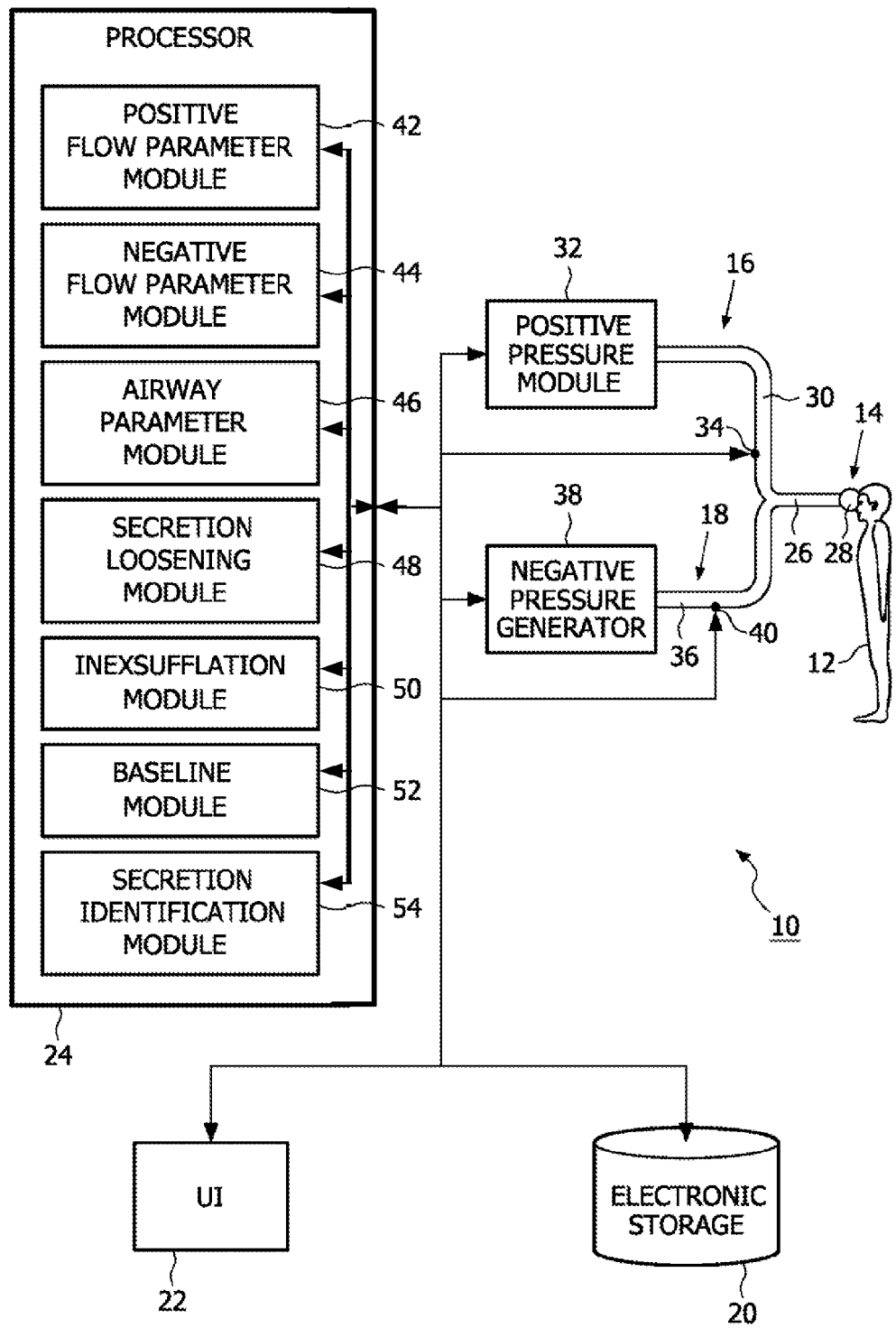
FIG. 1 schematically illustrates a system configured to insufflate-exsufflate a subject, in accordance with one or more embodiments of the invention.

FIG. 1 illustrates a system 10 configured to insufflate-exsufflate ("inexsufflate") a subject 12. The configuration of the components of system 10 enable subject 12 to be inexsufflated with an enhanced efficiency, with an enhanced precision, with an enhanced convenience to users (e.g., caregivers, etc.), and/or with other enhancements. In particular, system 10 may be configured to execute a predetermined routine that first loosens secretions within subject 12 prior to moving the secretions up the airway (e.g., toward the mouth) through an inexsufflation routine.

In a first embodiment, system 10 initiates the loosening routine and/or the inexsufflation routine automatically based on parameters of gas flow through the airway of subject 12. In a second embodiment, system 10 monitors parameters of a flow of gas drawn from the airway of subject 12 during secretion loosening and/or inexsufflation. In a third embodiment, system 10 is a stand-alone inexsufflation device that provides only for inexsufflation of subject 12. In a fourth embodiment, system 10 provides inexsufflation functionality in conjunction with other functionality typically attributed to a ventilator capable of mechanically breathing for subject 12. System 10 may be implemented to inexsufflate subject 12 in instances in which subject 12 is being ventilated mechanically (e.g., by system 10 or a separate ventilator), and/or in instances in which subject 12 is not being mechanically ventilated. In a fifth embodiment, system 10 includes an interface circuit 14, a positive pressure generation circuit 16, a negative pressure generation circuit 18, electronic storage 20, a user interface 22, and a processor 24, among other components.

Interface circuit 14 is configured to carry gas to and receives gas from an airway of subject 12. In one embodiment, interface circuit 14 includes a conduit 26 and a subject interface appliance 28. Conduit 26 is a flexible conduit capable of conveying gas therethrough. Subject interface appliance 28 may include either an invasive or non-invasive appliance for communicating gas between conduit 26 and the airway of subject 12. For example, subject interface appliance 28 may include a nasal mask, nasal/oral mask, total face mask, nasal cannula, endotracheal tube, or tracheal tube. Subject interface appliance 28 may also include a headgear assembly, such as mounting straps or a harness, for removing and fastening interface appliance 28 to subject 12.

Positive pressure generation circuit 16 is configured to controllably generate a positive pressure. The positive pressure generated by positive pressure generation circuit 16 may be delivered to the airway of subject 12 by interface circuit 14, resulting in a positive pressure in the airway of subject 12. In one embodiment, positive pressure generation circuit 16 includes a conduit 30 and a positive pressure generator 32.

Conduit 30 is a conduit (e.g., a flexible conduit) that communicates gas between positive pressure generator 32 and interface circuit 14. For example, conduit 30 may be connectable, at opposite ends, to conduit 26 of interface circuit 14 and positive pressure generator 32.

Positive pressure generator 32 controllably generates a positive pressure that is delivered to conduit 30. In one embodiment, positive pressure generator 32 includes one or more sources of pressurized gas, and one or more valves for controlling the release of the pressurized gas from positive pressure generator 32. By way of non-limiting example, the one or more sources of pressurized gas may include one or more of a wall-gas source, a blower, a pressurized tank or canister of gas, a piston, a diaphragm, and/or other pressurized sources of gas. In one embodiment, the one or more sources of pressurized gas include two or more separate sources of gases having different compositions that are mixed (e.g., in predetermined concentrations) within positive pressure generator 32. For example, the one or more sources of pressurized gas may include air and oxygen.

In one embodiment, system 10 includes one or more sensors 34 in communication with gas within positive pressure generation circuit 16. Sensors 34 are configured to generate output signals that convey information related to one or more parameters of the gas within positive pressure generation circuit 16. The one or more parameters may include one or more of a pressure, a flow rate, concentration(s) of one or more analytes within the gas, a flow profile, a pressure profile, and/or other parameters. Although sensors 34 are illustrated as being located at conduit 30, this is solely for illustrative purposes. In one embodiment at least one of sensors 34 is disposed in communication with gas within positive pressure generator 32.

Negative pressure generation circuit 18 is configured to controllably generate a negative pressure. The negative pressure may be communicated with the airway of subject 12 via interface circuit 14, thereby drawing a flow of gas from the airway of subject 12. In one embodiment, negative pressure generation circuit 18 includes a conduit 36 and a negative pressure generator 38.

Conduit 36 is a conduit (e.g., a flexible conduit) that communicates gas between negative pressure generator 38 and interface circuit 14. For example, conduit 36 may be connectable, at opposite ends, to conduit 26 of interface circuit 14 and negative pressure generator 38. It should be appreciated that although FIG. 1 depicts system 10 as a two-limbed ventilation system, in some embodiments, system 10 is implemented as a single-limbed system in which conduits 30 and 36 are embodied in the same physical conduit.

Negative pressure generator 38 controllably generates a negative pressure that is communicated to conduit 36. In one embodiment, negative pressure generator 38 includes one or more sources of negative pressure, and/or one or more valves that control the communication of the negative pressure to conduit 36. By way of non-limiting example, negative pressure generator 38 may include one or more of a blower, a vacuum pump, venturi, piston, diaphragm, wall vacuum source, and/or other sources of negative pressure. In one embodiment, conduit 36 is connected at one end to the inlet of positive pressure generator 32, and negative pressure generator 38 includes the same device (e.g., a blower) as positive pressure generator 32.

In one embodiment, system 10 includes one or more sensors 40 in communication with gas within negative pressure generation circuit 18. Sensors 40 are configured to generate output signals that convey information related to one or more parameters of the gas within negative pressure generation circuit 18. The one or more parameters may include one or more of a pressure, a flow rate, concentration(s) of one or more analytes within the gas, a flow profile, a pressure profile, and/or other parameters. Although sensors 40 are illustrated as being located at conduit 36, this is solely for illustrative purposes. In one embodiment, at least one of sensors 40 is disposed in communication with gas within negative pressure generator 38. Further, one or more of sensors 40 or sensors 34 may be in communication with gas disposed within interface circuit 26.

In one embodiment, electronic storage 20 comprises electronic storage media that electronically stores information. The electronic storage media of electronic storage 20 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 20 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 20 may store software algorithms, information determined by processor 24, information received via user interface 22, information related to signals generated by sensors 34 and/or sensors 40, and/or other information that enables system 10 to function properly. Electronic storage 20 may be a separate component within system 10, or electronic storage 20 may be provided integrally with one or more other components of system 10 (e.g., processor 24).

User interface 22 is configured to provide an interface between system 10 and a user (e.g., a caregiver to subject 12, subject 12, etc.) through which the user may provide information to and receive information from system 10. This enables data, results, and/or instructions and any other communicable items, collectively referred to as "information," to be communicated between the user and one or more of positive pressure generation circuit 32, negative pressure generation circuit 38, processor 24, and/or other components of system 10. Examples of interface devices suitable for inclusion in user interface 22 include a keypad, buttons, switches, a keyboard, knobs, levers, a display screen, a touch screen, speakers, a microphone, an indicator light, an audible alarm, and a printer. In one embodiment, user interface 22 actually includes a plurality of separate interfaces.

It should be understood that other communication techniques, either hard-wired or wireless, are also contemplated by the present invention as user interface 22. For example, the present invention contemplates that user interface 22 may be integrated with a removable storage interface provided by electronic storage 20. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 include, but are not limited to, an RS-232 port, RF link, an IR link, modem (telephone, cable or other). In short, any technique for communicating information with system 10 is contemplated by the present invention as user interface 22.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device, or processor 24 may represent processing functionality of a plurality of devices operating in coordination.

As is shown in FIG. 1, in one embodiment, processor 24 includes a positive flow parameter module 42, a negative flow parameter module 44, an airway parameter module 46, a secretion loosening module 48, an inexsufflation module 50, a baseline module 52, a secretion detection module 54, and/or other modules. Modules 42, 44, 46, 48, 50, 52, and/or 54 may be implemented in software; hardware; firmware; some combination of software, hardware, and/or firmware; and/or otherwise implemented. It should be appreciated that although modules 42, 44, 46, 48, 50, 52, and 54 are illustrated in FIG. 1 as being co-located within a single processing unit, in implementations in which processor 24 includes multiple processing units, modules 42, 44, 46, 48, 50, 52, and/or 54 may be located remotely from the other modules. Further, the description of the functionality provided by the different modules 42, 44, 46, 48, 50, 52, and/or 54 described below is for illustrative purposes, and is not intended to be limiting, as any of modules 42, 44, 46, 48, 50, 52 and/or 54 may provide more or less functionality than is described. For example, one or more of modules 42, 44, 46, 48, 50, 52 and/or 54 may be eliminated, and some or all of its functionality may be provided by other ones of modules 42, 44, 46, 48, 50, 52 and/or 54. As another example, processor 24 may include one or more additional modules that may perform some or all of the functionality attributed below to one of modules 42, 44, 46, 48, 50, 52, and/or 54.

Positive flow parameter module 42 is configured to determine one or more parameters of the gas within positive pressure generation circuit 16 or the airway of subject 12. The determination of the one or more parameters of the gas within positive pressure generation circuit 16 is determined based on the output signals generated by sensors 34, which are communicated within system 10 from sensors 34 to processor 24. The one or more parameters determined by positive flow parameter module 42 may include one or more of a pressure, a flow rate, concentration(s) of one or more analytes within the gas, a flow profile, a pressure profile, airway resistance, lung compliance, respiratory volume, and/or other parameters.

Negative flow parameter module 44 is configured to determine one or more parameters of the gas within negative pressure generation circuit 18. The determination of the one or more parameters of the gas within negative pressure generation circuit 18 is determined based on the output signals generated by sensors 40, which are communicated within system 10 from sensors 40 to processor 24. The one or more parameters determined by negative flow parameter module 44 may include one or more of a pressure, a flow rate, concentration(s) of one or more analytes within the gas, a flow profile, a pressure profile, airway resistance, lung compliance, respiratory volume, and/or other parameters.

Airway parameter module 46 is configured to determine one or more parameters of the gas within the airway of subject 12. The determination of the one or more parameters made by airway parameter module 46 may be made based on parameters of gas within one or both of positive pressure generation circuit 16 and/or negative pressure generation circuit 48, based on output signals generated by sensors 34 and/or 40, based on direct measurements of sensors disposed at or near the airway of subject 12 (not shown), or otherwise determined. The one or more parameters determined by airway parameter module 46 may include one or more of a pressure, a flow rate, concentration(s) of one or more analytes within the gas, a flow profile, a pressure profile, airway resistance, lung compliance, respiratory volume, and/or other parameters.

Secretion loosening module 48 is configured to automatically control positive pressure generation circuit 16 and negative pressure generation circuit 18 to deliver gas to and/or draw gas from the airway of subject 12 in accordance with a predetermined loosening routine. The loosening routine is designed to loosen secretions in the airway of subject 12 without moving substantial amounts of the secretions up the airway of subject 12. In order to loosen secretions, one embodiment of the present invention contemplates that providing a loosening routine in which the pressure and/or flow of gas within the airway of subject 12 varies in a periodic manner for a plurality of loosening cycles to cause gas to flow back and forth within the airway of subject 12, thereby loosening secretions.

In one embodiment, secretion loosening module 48 automatically controls one or both of the pressure and/or the flow rate of gas at the airway of subject 12 such that for a given loosening cycle, a minimum pressure and a maximum pressure, and/or a minimum flow rate and a maximum flow rate, are achieved over a cycle period. The cycle periods of a loosening routine may be predetermined. In one embodiment, the profile of one or both of the flow between the minimum and maximum flow rate and/or the pressure between the minimum and maximum pressure over a given loosening cycle are predetermined.

Inexsufflation module 50 is configured to automatically control positive pressure generation circuit 16 and negative pressure generation circuit 18 to deliver gas to and/or draw gas from the airway of subject 12 in accordance with an inexsufflation routine. The inexsufflation routine is designed to move secretions up from the airway of subject 12 (e.g., toward the mouth) so that the secretions can be removed from the airway of subject 12. To move the loosened secretions up the airway, inexsufflation module 50 causes the pressure and/or flow of gas within the airway of subject 12 to vary in a periodic manner for one or more inexsufflation cycles.

In one exemplary embodiment, inexsufflation module 50 automatically controls one or both of the pressure and/or the flow rate of gas at the airway of subject 12 such that for a given inexsufflation cycle, a minimum pressure and/or a maximum pressure, and/or a minimum flow rate and a maximum flow rate, are achieved over a cycle period. The cycle period(s) of the inexsufflation cycle(s) of an inexsufflation routine may be predetermined. In one embodiment, the profile of one or both of the flow between the minimum and maximum flow rate and/or the pressure between the minimum and maximum pressure over a given inexsufflation cycle are predetermined. As should be appreciated, during an inexsufflation cycle, the differential between the minimum and maximum pressures creates transient flow out of the airway of subject 12 (i.e., negative flow) that draws the secretions up the airway of subject 12. Because this flow provides the motive force of the inexsufflation cycle, in one embodiment, the minimum flow rate of the gas is predetermined (e.g., higher will tend to draw more secretions further up the airway), and the maximum flow rate is of less concern.

Figure 2:
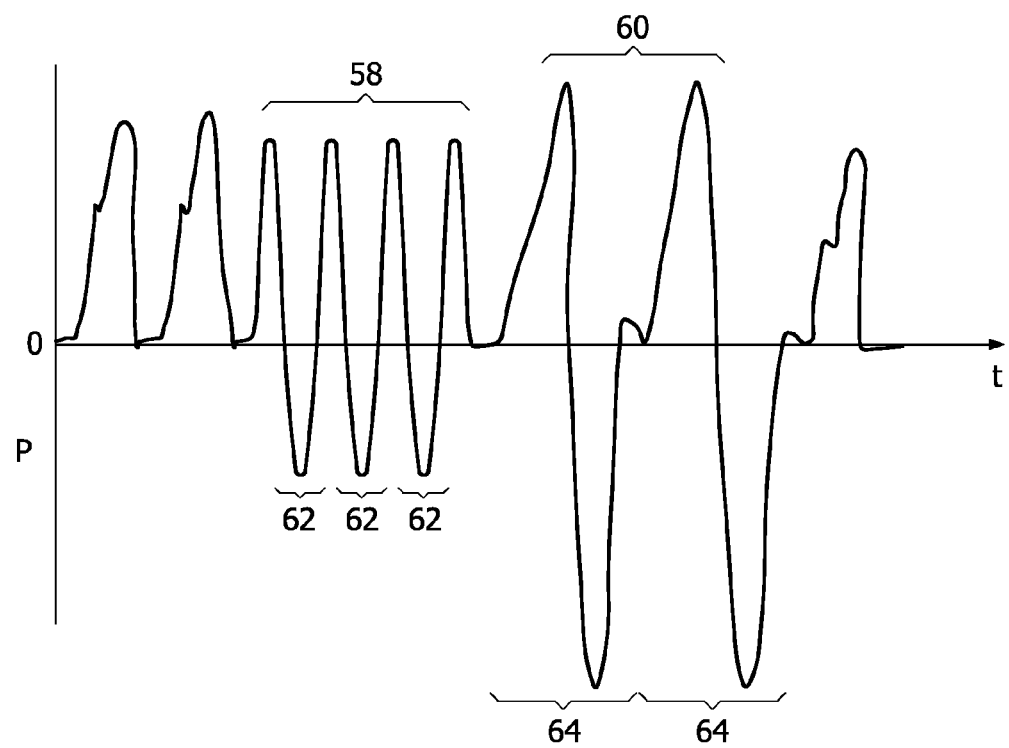
FIG. 2 illustrates a plot of the pressure of gas at the airway of a patient during a loosening and insufflation-exsufflation routine, according to one or more embodiments of the invention.

Because inexsufflation cycles are designed to move secretions up the airway, rather than just loosen secretions like loosening cycles, the changes in pressure and/or flow rate of gas at the airway of subject 12 during inexsufflation cycles will be more extreme and/or extended than the oscillations during loosening cycles. In particular, negative flows will typically be more extreme to move secretions along the airway by generating a simulated cough. By way of illustration, FIG. 2 shows a plot of a pressure profile of gas at the airway of a subject. The profile includes pressures present at the airway of the subject during a loosening routine 58 and an inexsufflation routine 60.

As can be seen in FIG. 2, loosening routine 58 includes a plurality of loosening cycles 62, with each loosening cycle including a minimum pressure and a maximum pressure, and taking place over a cycle period. Similarly, inexsufflation routine 60 includes a plurality of inexsufflation cycles 64. At each inexsufflation cycle 64, a maximum pressure and a minimum pressure is achieved over a cycle period.

The relatively short cycle periods of loosening routine 58 are designed to cause secretions within the airway of the subject to be loosened by fluctuations in pressure and the corresponding flow of gas back and forth through the airway. However, since the flows caused by the pressures generated during loosening routine 58 are relatively low and balanced (between the positive and negative flows), substantial amounts of the loosened secretions are not moved up the airway during loosening routine 58. Loosening secretions in this manner prior to commencing inexsufflation routine 60 may enhance the amount of secretions that are eventually extracted from the airway of the subject.

In contrast, the cycle periods of inexsufflation routine 60 are relatively protracted, and the minimum pressure and/or the maximum pressure achieved during inexsufflation cycles 64 tend to be more extreme than those achieved during loosening cycles 62. The protracted cycle periods and extreme pressure minimums and maximums create a series of high cough-like gas flows that enables the gas flowing through the airway to actually draw loosened secretions up of the airway of subject 12. In particular, pressure differentials at the airway of the subject will be more extreme (e.g., with a larger difference between the maximum and the minimum) and/or more protracted for inexsufflation routine 60, as this will produce the requisite transient high flows to move the secretions out of the airway of the subject.

Figure 3:
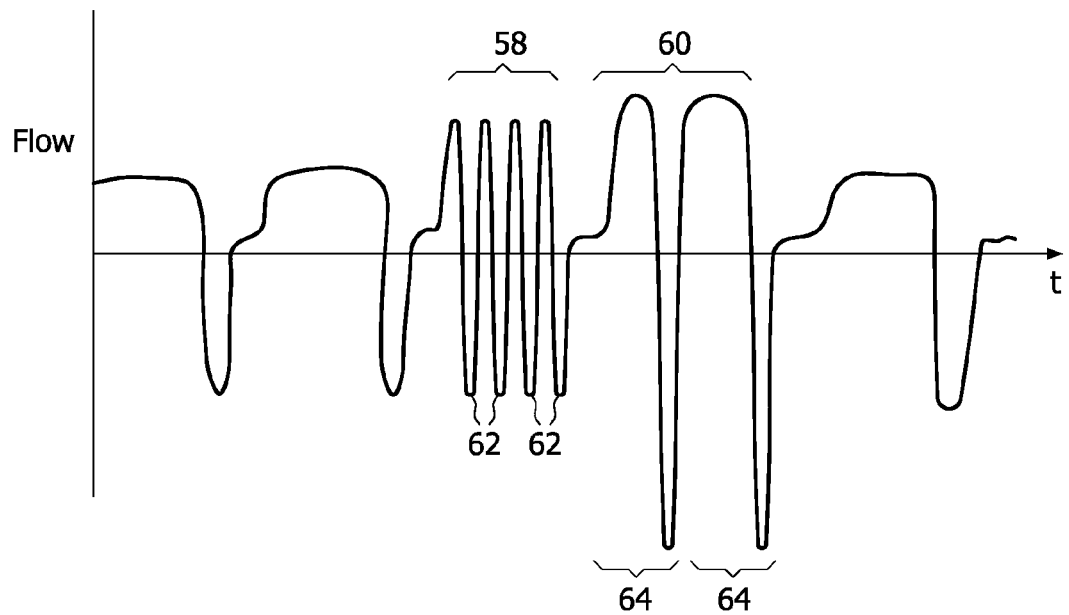
FIG. 3 illustrates a plot of the flow rate of gas at the airway of a patient during a loosening and insufflation-exsufflation routine, in accordance with one or more embodiments of the invention.

FIG. 3 shows a plot of a flow rate profile of the gas through the airway of the patient during loosening routine 58 and inexsufflation routine 60. As can be seen in FIG. 3, each loosening cycle 62 includes a minimum flow rate and a maximum flow rate. Similarly, at each inexsufflation cycle 64, a maximum flow rate and a minimum flow rate is achieved over a cycle period. As was the case with pressure, the extremes of the flow rate, particularly the minimum flow rate, which is a flow gas exhaled from the lungs of the subject, are more extreme for the inexsufflation cycles 64 than for the loosening cycles 62. This enhances the movement of secretions up the airway of the subject, as the secretions are first loosened during loosening routine 58 before being extracted by the relatively extreme minimum flow rates created during inexsufflation routine 60.

Referring back to FIG. 1, in controlling positive pressure generation circuit 16 and/or negative pressure generation circuit 18 in accordance with a loosening routine and an inexsufflation routine, secretion loosening module 48 and/or inexsufflation module 50 implement one or more gas parameters determined by one or more of positive flow parameter module 42, negative flow parameter module 44, and/or airway parameter module 46. In particular, the implementation of parameters determined by negative flow parameter module 44 and/or airway parameter module 46 may provide enhancements over conventional systems, which do not include sensors that enable accurate determinations of these parameters.

By way of example, in one embodiment, negative pressure parameter module 44 determines a flow rate and/or a pressure of gas within negative pressure generation circuit 18. This enables secretion loosening module 48 and inexsufflation module 50 to precisely control pressure, pressure profile, flow rate, flow profile, and/or volume of the gas extracted from the airway of subject 12 via negative pressure generation circuit 18. By contrast, conventional inexsufflation systems do not determine these parameters of the gas extracted from subject 12, and only provide for an inexsufflation cycle that is controlled based on a predetermined timing (e.g., positive pressure for a predetermined amount of time, negative pressure for a predetermined amount of time) and preset positive and negative pressures. Due to the parameter(s) of the gas within negative pressure generation circuit 18 that are available to secretion loosening module 48 and inexsufflation module 50, the loosening routines and/or inexsufflation routines executed by secretion loosening module 48 inexsufflation module 50 can be tailored to provide gas to and extract gas from the airway of subject 12 to extract secretions in a more effective, comfortable, and/or automated manner.

Baseline module 52 is configured to ensure that a key parameter of gas in system 10 and/or in the respiratory system of subject 12 does not cross a baseline measurement. For example, the key parameter may include one or more of a pressure within the respiratory system of subject 12, a flow rate at the airway of subject 12, a volume within the respiratory system of subject 12, and/or other parameters. Keeping the key parameter of gas in system 10 and/or the respiratory system of subject 12 from crossing the baseline measurement may enhance the comfort of the patient, the effectiveness of the inexsufflation, the effectiveness of the ventilation, and/or other aspects of the inexsufflation and/or ventilation.

Baseline module 52 may configure the loosening routine and/or the inexsufflation routine implemented by secretion loosening module 48 and/or inexsufflation module 50 to ensure that the key parameter does not cross the baseline measurement. In one embodiment, baseline module 52 determines the loosening routine and/or the inexsufflation routine including one or more of a maximum pressure, a minimum pressure, a maximum flow rate (e.g., a maximum insufflation flow rate), a minimum flow rate (e.g., a maximum exsufflation flow rate), a pressure profile, a flow profile, an insufflation volume, an exsufflation volume, and/or other parameters of the loosening routine and/or the inexsufflation routine such that the key parameter does not cross the baseline measurement.

By way of non-limiting example, where the key parameter is a minimum pressure in the lungs of subject 12, baseline module 52 may configure the loosening routine and/or the inexsufflation routine such that the volume of gas provided to the lungs of subject 12 during a cycle of loosening and/or inexsufflation has a predetermined relationship with the volume of gas removed from the lungs of subject 12 during the same cycle of loosening and/or inexsufflation. For instance, the volume of gas provided may be greater than (e.g., by a predetermined amount) the volume of gas removed, substantially equal to the volume of gas removed, or less than the volume of gas removed by a predetermined amount that enables the lungs of subject 12 to maintain a pressure that is controlled in relation to the baseline pressure.

Baseline module 52 may monitor the provision of therapy to subject 12 during loosening and/or inexsufflation by secretion loosening module 48 and/or inexsufflation module 50, and dynamically adjust one or more of the pressure, flow rate, and/or other parameters of the gas provided to and/or drawn from subject 12 to ensure that the baseline measurement is not crossed. For example, where the key parameter is a minimum pressure in the lungs of subject 12, baseline module 52 may monitor the volume (e.g., through a flow rate) of the gas provided to and/or drawn from the airway of subject 12. Based on this monitoring, baseline module 52 may dynamically alter the therapy provided to subject 12 should the volume of gas drawn from the airway of subject 12 reach (or approach) some predetermined relationship with the volume of gas previously provided to the airway of subject 12. The predetermined relationship between the volumes of gas provided to and drawn from the airway of subject 12 may be a predetermined difference (e.g., a predetermined amount by which the volume provided to the airway exceeds the volume drawn from the airway), or a substantial equivalence.

It should be appreciated that some or all of the functionality of baseline module 52 is facilitated by parameters determined by one or more of modules 42, 44, and/or 46. In particular, parameters determined based on output signals generated by sensors 40 associated with negative pressure generation circuit 18 (e.g., determined by one or both of modules 44 and/or 46) provide information to baseline module 52 that may not be available in conventional inexsufflation systems.

In one embodiment, the key parameter and/or the baseline measurement vary on a subject-by-subject and/or treatment-by-treatment basis. To accommodate this, one or both of the key parameter and/or the baseline measurement are selectably configurable by a user (e.g., a caregiver). The user is provided with a mechanism for configuring the key parameter and/or the baseline measurement through user interface 22. For example, user interface 22 may include a graphical user interface that enables the user to select a key parameter and/or input or adjust a baseline measurement for the key parameter. It should be appreciated that the discussion of a key parameter above is not intended to be limiting in that a plurality of key parameters with corresponding baseline measurements may be implemented by baseline module 52.

Secretion detection module 54 is configured to monitor one or more parameters of gas provided to the airway of subject 12 and/or received from the airway of subject 12 during ventilation to automatically identify an accumulation of secretions in the airway of subject 12. In one embodiment, system 10 is configured such that an identification of an accumulation of secretions in the airway of subject 12 by secretion detection module 54 triggers an inexsufflation routine to move the identified accumulation up the airway. For example, an identification of secretions in the airway of subject 12 may trigger activation of a loosening routine conducted by secretion loosening module 48, followed by an inexsufflation routine conducted by inexsufflation module 50. In one embodiment, the identification of an accumulation of secretions in the airway of subject 12 may further trigger a notification to a caregiver that an inexsufflation routine has been performed, and the secretions moved up the airway during the routine will need to be removed. In one embodiment, the trigger of an inexsufflation routine by the identification of secretions in the airway of subject 12 includes notifying a user (e.g., subject 12, a caregiver, etc.) of the trigger, and requires a manual authorization from the user before commencing the inexsufflation routine. For example, the notification and/or authorization may be communicated between the user and processor 24 via user interface 22.

The one or more parameters monitored by secretion detection module 54 may include one or more of an airway resistance, a lung compliance, a flow rate, a flow profile, a pressure profile, a maximum pressure, breathing sounds, and/or other parameters. In one embodiment, secretion detection module 54 identifies an accumulation of secretions in the airway of subject 12 based on a comparison between a parameter and a predetermined threshold. The threshold may be configurable by a user (e.g., through user interface 22). In one embodiment, detection module 54 identifies an accumulation of secretions in the airway of subject 12 based on a data matching threshold that matches one or more of the parameters (e.g., flow profile, pressure profile, etc.) with a predetermined pattern or waveform.

Figure 4:
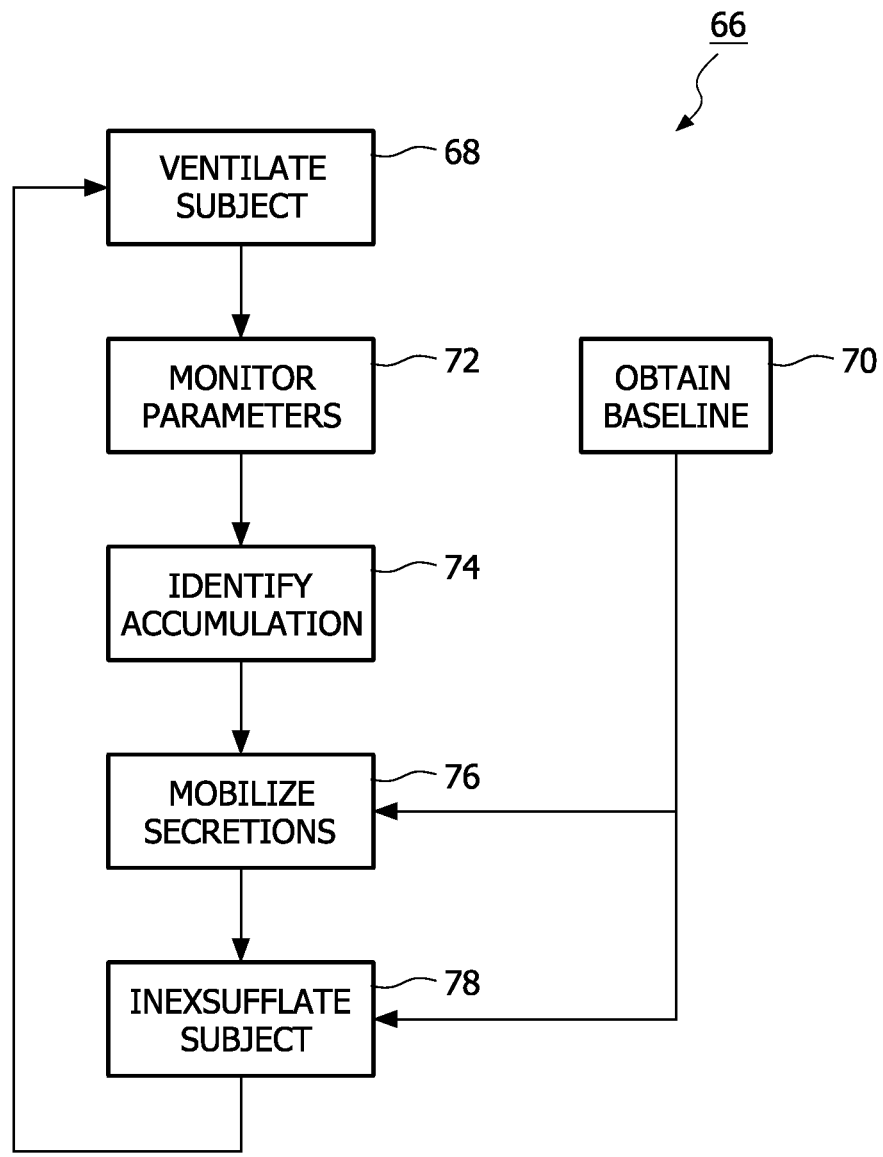
FIG. 4 illustrates a method of insufflate-exsufflating a subject, in accordance with one or more embodiments of the invention.

FIG. 4 illustrates a method 66 of inexsufflating a subject. The operations of method 66 presented below are intended to be illustrative. In some embodiments, method 66 may be accomplished with one or more additional operations not described, and/or without one or more of the operations discussed. Additionally, the order in which the operations of method 66 are illustrated in FIG. 4 and described below is not intended to be limiting.

In some embodiments, method 66 may be implemented by a system having components similar to those described above with respect to system 10 (shown in FIG. 1). However, this does not limit the disclosure below, as method 66 may be implemented in a variety of other contexts and/or systems that those previously set forth.

At an operation 68, the subject is ventilated. The ventilation may be through an intubation, mask, or other interface appliance. In one embodiment, the ventilation is performed by a positive pressure generation circuit that is the same as, or similar to, positive pressure generation circuit 16 (shown in FIG. 1 and described above). The positive pressure generation circuit may be included in the same system eventually used to inexsufflate the subject, or may be part of a separate system that is releasably connected to an interface circuit that delivers gas from the positive pressure generation circuit to the airway of the subject.

At an operation 70, a key parameter and/or baseline measurement for the key parameter are obtained. The baseline measurement of the key parameter corresponds to a level of the key parameter that will not be crossed during inexsufflation of the subject. In one embodiment, operation 70 is performed by a baseline module that is the same as, or similar to, baseline module 52 (shown in FIG. 1 and described above).

At an operation 72, one or more parameters of the gas delivered to the airway of the subject and/or received from the airway of the subject during ventilation are monitored. The one or more parameter may include one or more of an airway resistance, a flow rate, a flow profile, a pressure profile, and/or other parameters. In one embodiment, operation 72 is performed by a secretion identification module that is the same as, or similar to, secretion identification module 54.

At an operation 74, an identification of an accumulation of secretions within the airway of the subject are identified based on the parameters monitored at operation 72. In one embodiment, operation 74 is performed by the secretion identification module.

At an operation 76, a loosening routine is initiated in response to the identification made at operation 74. The loosening routine automatically oscillates the pressure and/or flow at the airway of the subject in order to loosen the accumulated secretions without substantial amounts of the secretions. In one embodiment, operation 76 is performed by a secretion loosening module that is the same as, or similar to, secretion loosening module 48 (shown in FIG. 1 and described above).

At an operation 78, an inexsufflation routine is initiated in response to the identification made at operation 74. The inexsufflation routine automatically controls the pressure and/or flow at the airway of the subject in order to extract the accumulated secretions. In one embodiment, operation 78 is performed by an inexsufflation module that is the same as, or similar to, inexsufflation module 50 (shown in FIG. 1 and described above).

Throughout one or both of operations 76 and/or 78, one or more parameters of the gas provided to and/or removed from the airway of the subject are monitored to ensure that the baseline measurement of the key parameter obtained at operation 70 is not crossed. This functionality during operation 76 and/or operation 78 may be provided by the baseline module.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system to extract secretions from the airway of a subject, the system comprising:
   (a) a circuit to control the pressure at the airway of a subject by generating a flow of gas having a controlled pressure that is delivered to the airway of the subject by an airway interface that communicates the circuit with the airway of the subject; and
   (b) a processor to control the circuit such that the flows of gas generated by the circuit move secretions up the airway of the subject by:
   (1) use of a secretion loosening module for fluctuating the pressure in the airway of the subject up and down between positive and negative pressures for a plurality of loosening cycles such that the fluctuation of the pressure in the airway of the subject during the loosening cycles loosens secretions in the airway of the subject without moving the secretions up the airway of the subject, followed by
   (2) use of an inexsufflation module for fluctuating the pressure in the airway of the subject up and down for one or more insufflation-exsufflation cycles such that a given insufflation-exsufflation cycle insufflates and exsufflates the subject, thereby moving secretions up the airway of the subject.

2. The system of claim 1, wherein the processor controls the circuit such that:
   a loosening cycle of the plurality of loosening cycles causes gas to flow within the airway of the subject at a minimum flow rate at some point during the loosening cycle and an insufflation-exsufflation cycle of the one or more insufflation-exsufflation cycles causes gas to flow within the airway of the subject at a minimum flow rate at some point during the insufflation-exsufflation cycle, and
   a lowest minimum flow rate of any of the plurality of loosening cycles is greater than a highest minimum flow rate of any of the one or more insufflation-exsufflation cycles.

3. The system of claim 2, wherein the processor controls the circuit such that the loosening cycle causes gas to flow within the airway of the subject at a maximum flow rate at some point during the loosening cycle, and wherein the gas moving through the airway of the subject at the minimum and maximum flow rates of the loosening cycle loosen secretions in the airway of the subject without substantially moving the loosened secretions in the airway of the subject.

4. The system of claim 1, wherein the processor controls the circuit such that:
   a loosening cycle of the plurality of loosening cycles takes place over a cycle period corresponding to the loosening cycle and an insufflation-exsufflation cycle takes place over a cycle period corresponding to the insufflation-exsufflation cycle, and
   the cycle period corresponding to any of the plurality of loosening cycles is less than the cycle period corresponding to any of the one or more insufflation-exsufflation cycles.

5. The system of claim 1, wherein the processor controls the circuit such that the one or more insufflation-exsufflation cycles occurs immediately after the plurality of loosening cycles.

6. The system of claim 1, further comprising:
   one or more sensors in communication with gas within the circuit that generate output signals conveying information related to one or more additional parameters of the gas within the circuit in addition to information related to the pressure of the gas within the circuit, wherein the processor further controls the circuit to insufflate-exsufflate the subject, wherein responsive to the processor receiving the output signals generated by the one or more sensors, the processor implements information conveyed in the one or more output signals related to the one or more additional parameters of the gas within the circuit in controlling the circuit during insufflation-exsufflation.

7. The system of claim 6, wherein the one or more additional parameters of the gas include one or more of a flow rate, a volume, a flow profile, or a pressure profile.

8. The system of claim 6, wherein the processor implements information conveyed in one or more output signals related to the one or more additional parameters to control at least one of the one or more additional parameters of the gas in the circuit.

9. The system of claim 6, wherein the processor further determines a baseline measurement for one or more key parameters of gas in the respiratory system of the subject; and controls the circuit to insufflate-exsufflate the subject such that one or more key parameters of the gas in the respiratory system of the subject do not breach the baseline measurement.

10. The system of claim 9, further comprising a user interface that enables the user to input the baseline measurement to the processor.

11. The system of claim 9, wherein the one or more key parameters include at least one of pressure and volume.

12. A method of extracting secretions from the airway of a subject, the method comprising steps of:
loosening secretions within the airway of a subject, via a processor controlled gas flow and pressure circuit, without extracting amounts of secretions by delivering gas to the airway of the subject such that pressure in the airway of the subject is fluctuated up and down between positive and negative pressures for a plurality of loosening cycles; and followed by
insufflating-exsufflating the subject, via the processor controlled gas flow and pressure circuit, to extract secretions from the airway of the subject by delivering gas to the airway of the subject such that pressure in the airway alternates the pressure in the airway of the subject between positive pressure and negative pressure for one or more insufflation-exsufflation cycles, thereby extracting secretions from the airway of the subject.

13. The method of claim 12, wherein a loosening cycle of the plurality of loosening cycles causes gas to flow within the airway of the subject at a minimum flow rate at some point during the loosening cycle and an insufflation-exsufflation cycle of the one or more insufflation-exsufflation cycles causes gas to flow within the airway of the subject at a minimum flow rate at some point during the insufflation-exsufflation cycle, and wherein a lowest minimum flow rate of any of the plurality of loosening cycles is greater than a highest minimum flow rate of any of the one or more insufflation-exsufflation cycles.

14. The method of claim 13, wherein the loosening cycle causes gas to flow within the airway of the subject at a maximum flow rate at some point during the loosening cycle, and wherein the gas moving through the airway of the subject at the minimum and maximum flow rates of the loosening cycle loosen secretions in the airway of the subject without substantially moving the loosened secretions in the airway of the subject.

15. The method of claim 12, wherein a loosening cycle of the plurality of loosening cycles takes place over a cycle period corresponding to the loosening cycle and an insufflation-exsufflation cycle of the one or more insufflation-exsufflation cycles takes place over a cycle period corresponding to the insufflation-exsufflation cycle, and wherein the cycle period corresponding to any of the plurality of loosening cycles is less than the cycle period corresponding to any of the one or more insufflation-exsufflation cycles.

16. The method of claim 12, wherein the one or more insufflation-exsufflation cycles occurs immediately after the plurality of loosening cycles.

17. The method of claim 12, further for insufflating-exsufflating the subject comprising steps of:
(a) controlling, via the processor controlled gas flow and pressure circuit, the flow of gas in the airway of the subject to insufflate-exsufflate the subject by generating a flow of gas having a controlled pressure that is delivered to the airway of the subject;
(b) monitoring, via one or more sensors, one or more parameters of the gas within the circuit in addition to information related to the pressure of the gas within the circuit; and
(c) adjusting the operation of the circuit during the insufflation-exsufflation of the subject based on the one or more parameters of the gas within the circuit.

18. The method of claim 17, wherein the one or more parameters of the gas within the circuit include one or more of a flow rate, a volume, a flow profile, or a pressure profile.

19. The method of claim 17, wherein the step of adjusting the operation of the circuit during the insufflation-exsufflation of the subject comprises adjusting the operation of the circuit to control at least one of the one or more parameters of the gas in the circuit.

20. A system configured to insufflate-exsufflate a subject, the system comprising:
(a) a circuit to control the pressure at the airway of a subject by generating a flow of gas having a controlled pressure that is delivered to the airway of the subject by an airway interface that communicates the circuit with the airway of the subject;
(b) one or more sensors to generate one or more output signals that convey information related to one or more parameters of gas within the airway of the subject; and
(c) a processor to receive the one or more output signals, and to control the circuit to insufflate-exsufflate the subject, the processor comprising:
(1) a secretion detection module to monitor the information related to one or more parameters of the gas within the airway of the subject and to identify an accumulation of secretions in the airway of the subject based on the information related to one or more parameters of the gas within the airway of the subject; and
(2) an inexsufflation module to control the circuit to commence an insufflation-exsufflation routine that insufflate-exsufflates the subject based on identifications of accumulated secretions in the airway of the subject by the secretion detection module such that identification of secretions in the airway of the subject by the secretion detection module trigger the inexsufflation module to control the circuit to commence an insufflation-exsufflation routine without intervention from a user, the insufflation-exsufflation routine including (i) secretion loosening via a plurality of loosening cycles, with each loosening cycle fluctuating the pressure in the airway of the subject up and down between positive and negative pressures, the plurality of loosening cycles followed by (ii) inexsufflation via one or more insufflation-exsufflation cycles.

* * * * *